United States Patent [19]

Bosemark et al.

[11] Patent Number: 5,639,951
[45] Date of Patent: Jun. 17, 1997

[54] DOUBLED HAPLOIDS

[75] Inventors: Nils Olof Bosemark, Ängelholm, Sweden; Benedikt R. V. L. Timmerman, Belberaud, France

[73] Assignee: Sandoz Ltd., Basel, Switzerland

[21] Appl. No.: 269,701

[22] Filed: Jul. 1, 1994

[30] Foreign Application Priority Data

Jul. 6, 1993 [GB] United Kingdom .................. 9313975

[51] Int. Cl.$^6$ .................. C12N 15/29; C12N 15/82; A01H 1/02; A01H 1/04; A01H 5/00
[52] U.S. Cl. .................. 800/205; 800/200; 800/235; 800/250; 800/DIG. 56; 47/58; 47/DIG. 1; 536/23.6; 435/172.3
[58] Field of Search .................. 47/58, 58.01, 58.03, 47/DIG. 1; 800/200, 205, 235, 250, DIG. 56; 435/172.3; 536/23.6

[56] References Cited

U.S. PATENT DOCUMENTS

| | | | |
|---|---|---|---|
| 4,425,737 | 1/1984 | Henke | 47/58 |
| 5,084,082 | 1/1992 | Sebastian | 71/90 |

FOREIGN PATENT DOCUMENTS

| | | | |
|---|---|---|---|
| 198288 | 3/1986 | European Pat. Off. | C12N 15/00 |
| 463999 | 6/1991 | European Pat. Off. | A01H 1/02 |
| 2139466 | 11/1984 | United Kingdom | A01G 7/00 |
| 2208346 | 3/1989 | United Kingdom | A01H 1/02 |

OTHER PUBLICATIONS

Barnatzky et al. "Using molecular markers to analyze genome organizations . . ." Plant Tissue and Cell Culture, 1987, pp. 331–339.

Poelman, J.M. 'Breeding Field Crops' 1986 pp. 102–106: "Haploidy"; pp. 157–167: Anther culture and haploid plant production.

Genovesi, A.D. "Maize (Zea Mays L.): In bitro production of haploids" 1990 Springer Verlag, Berlin, pp. 176–203, Chapter II.3.

Lashermes, P. et al. Theor Appl Genet. 76:570–572. Mar. 1988.

Genovesi, A.D. In Biotechnology in Agriculture and Forestry 12. Haploids in Crop Improvement I. Bajaj, Y. P. S., ed. Springer–Verlag, N.Y., N.Y. Ch. II.3:176–203. Oct. 1990.

Coe, E. H., Jr. et al. In Corn and Corn Improvement, Third Edition. Sprague, G. F. et al., eds. ASA–CSSA–SSSA. Madison, WI. p. 213. Jan. 1988.

Greenblatt, I. M. The Journal of Heredity. 58(1):9–13. Jan. 1967.

Peloquin, S. J. In Plant Breeding II. Frey, K. J., ed. The Iowa State University Press. Ames, IA. pp. 117–121. Jan. 1981.

*Primary Examiner*—David T. Fox
*Assistant Examiner*—Thomas Haas
*Attorney, Agent, or Firm*—Lynn Marcus-Wyner

[57] ABSTRACT

The present invention provides, inter alia, the use in the screening of haploid or doubled haploid plants or seeds of at least one dominant gene selected from the group consisting of conditional lethal genes, screenable marker genes and selectable marker genes. Preferably the haploids are induced by haploid inducing genes, such as "indeterminate gametophyte". The invention still further provides haploid plants comprising said at least one dominant gene, and a process for the production thereof, together with plants which result from said use and said process.

23 Claims, 2 Drawing Sheets

|  | ig IaaH | ig  - | Ig IaaH | Ig  - |
|---|---|---|---|---|
| ig IaaH | ig IaaH  ———  ig IaaH  MS    4 | ig IaaH  ———  ig  -  MS    4 | ig IaaH  ———  Ig IaaH  8 | ig IaaH  ———  Ig  -  8 |
| ig  - | ig  -  ———  ig IaaH  MS    4 | ig  -  ———  ig  -  MS    4 | ig  -  ———  Ig IaaH  8 | ig  -  ———  Ig  -  7 |
| Ig IaaH | Ig IaaH  ———  ig IaaH  8 | Ig IaaH  ———  ig  -  8 | Ig IaaH  ———  Ig IaaH  N.    6 | Ig IaaH  ———  Ig  -  N    6 |
| Ig  - | Ig  -  ———  ig IaaH  8 | Ig  -  ———  ig  -  7 | Ig  -  ———  Ig IaaH  N    6 | Ig  -  ———  Ig  -  N    6 |

= desired genotypes 4, 6, 7, 8 = See Example 1 in description

MS = Male sterile

N = Normal seed

|        | ig  Pat        | ig   -         | Ig  Pat        | Ig   -         |
|--------|----------------|----------------|----------------|----------------|
| ig  Pat | ig  Pat<br>―――<br>ig  Pat<br>MS    4 | ig  Pat<br>―――<br>ig   -<br>MS    4 | ig  Pat<br>―――<br>Ig  Pat<br>          8 | ig  Pat<br>―――<br>Ig   -<br>          8 |
| ig   -  | ig   -<br>―――<br>ig  Pat<br>MS    4 | ig   -<br>―――<br>ig   -<br>MS    4 | ig   -<br>―――<br>Ig  Pat<br>          8 | ig   -<br>―――<br>Ig   -<br>          7 |
| Ig  Pat | Ig  Pat<br>―――<br>ig  Pat<br>          8 | Ig  Pat<br>―――<br>ig   -<br>          8 | Ig  Pat<br>―――<br>Ig  Pat<br>N     6 | Ig  Pat<br>―――<br>Ig   -<br>N     6 |
| Ig   -  | Ig   -<br>―――<br>ig  Pat<br>          8 | Ig   -<br>―――<br>ig   -<br>          7 | Ig   -<br>―――<br>Ig  Pat<br>N     6 | Ig   -<br>―――<br>Ig   -<br>N     6 |

  = desired genotypes 4, 6, 7, 8    = See Example 4 in description

MS    = Male sterile

N    = Normal seed

Figure 2

DOUBLED HAPLOIDS

BACKGROUND OF THE INVENTION

The present invention relates to plant breeding. More particularly, the invention relates to the production of haploids and doubled haploids (whether at the whole plant or seed level)—preferably induced by a haploid inducing gene—and to the selection and/or screening therefor.

The mutant gene "indeterminate gametophyte" (ig), when present in the female parent results in offspring with a high proportion of defective seeds and a greatly enhanced frequency of haploids of both maternal and paternal origin. The ratio of maternal to paternal types is about 1:2. In crosses of maize plants with igig females to four standard inbreds it has been shown that the frequency of androgenesis ranges from about 0.5 to 2 percent with one androgenetic plant in 10 being diploid. However, the influence of the paternal donor is much stronger than hitherto thought. Thus, the average frequency of androgenesis due to ig has been shown to be as little as only 0.03%, with some genotypes perhaps reaching 1.5%. Recently, it has been suggested that placing the ig gene in an early maturing maize genotype, such as the inbred line Co220, should make the production of haploids easier whilst maintaining a similar or higher level of haploid induction. Even so, use of this procedure for large scale production of haploids in practical plant breeding requires an efficient marker system that permits discrimination between haploids and spontaneously doubled haploids of paternal origin on the one hand, and sexual diploids and maternal haploids and doubled haploids on the other hand.

The most reliable marker system hitherto used, at least in respect of maize, is a Purple Embryo Marker stock (PEM) of the genotype b p1 A C $R^{nj:cu\ du}$ pr $P^{wr}$, originally developed to detect maternal haploids, but used also in connection with ig-induced haploid detection. The critical gene in this system is the R-allele. $R^{nj:cu\ du}$, which in combination with the dominant pigment-conditioning genes A and C causes red or purple pigmentation of the aleurone, primarily on the crown portion of the kernel, and a deep purple pigmentation in the embryo. Any colorless-seed maize stock can function as the haploid donor parent provided it is not homozygous RR and the lack of color is not due to a dominant pigment inhibitor. For the detection of maternal haploids the PEM stock is used as the pollinator whilst for the detection of ig-induced androgenetic haploids a PEM-ig stock is used as the seed parent in crosses with the donor line or breeders stock. With both systems the desired haploids have a white embryo and colored aleurone. While the PEM system permits efficient selection of maternal haploids in the dry kernels, the high proportion of defective and small size kernels in igig females hampers seed selection of androgenetic haploids.

SUMMARY OF THE INVENTION

The present invention provides a marker system, which is substantially free of the above mentioned disadvantages, for use in the selection of haploids.

BRIEF DESCRIPTION OF THE DRAWINGS

FIG. 2 illustrates a segregating $S_1$ generation of maize plants and the use of the phosphinotricin acetyl transferase (PAT) gene and as further described in Example 4.

DETAILED DESCRIPTION OF THE INVENTION

Figure 1:
FIG. 1 illustrates a segregating $S_1$ generation of maize plants and the use of the Iaa gene in the selection of maize haploids and as further described in Example 1.

According to the present invention there is provided the use as a marker in the selection of haploids or doubled haploids of at least one of a dominant selectable marker gene, a dominant screenable marker gene or a dominant conditional lethal gene.

By "dominant conditional lethal gene" is meant any gene, the product of which is capable of directing the conversion of a non-lethal or non-inhibitory factor to a lethal or inhibitory factor. It is particularly preferred that the factor is a chemical, such as naphthaleneacetamide, chlorate, or indole-3-acetamide, for example, in which case the lethal gene may encode nitrate reductase (NR) or indoleacetamide hydrolase (IaaH).

By "dominant selectable marker gene" is meant any gene, the product of which is capable of directing the conversion of a toxic, inhibitory, or otherwise metabolism disturbing factor into a less toxic, less inhibitory or less disturbing such factor. It is preferred that the said gene product is capable of rendering the factor substantially non toxic or substantially non-inhibitory or otherwise disturbing. It is particularly preferred that the factor is a herbicide or antibiotic. Accordingly, the selectable marker gene may encode a herbicide inactivating enzyme, which for example is capable of conferring herbicide tolerance or resistance to the tissue containing it. Thus the selectable marker gene may encode phosphinotricin acetyl transferase (PAT), glyphosate oxidoreductase (COX), or EPSPS and thus confer tolerance or resistance to glufosinate or glyphosate for example (glufosinate is commercially obtainable from Hoechst AG under the trade name "BASTA").

By "dominant screenable marker gene" is meant any gene, the product of which is capable of providing in the tissue containing it a phenotypically observable characteristic. It is preferred that the said product is capable of acting on a substrate which—as a consequence of such action—is converted into a chromophore, fluorophore, or other compound capable of readily being identified, either directly or indirectly. It is particularly preferred that the screenable marker gene encodes a Beta glucuronidase which is capable of cleaving non-toxic glucuronide-fluorescein dyes thereby liberating such dyes which thus can be recognized, and quantified if necessary or desirable.

Such dominant genes may be used in the selection of haploids induced, for example, by haploid-inducing genes such as that conferring "indeterminate gametophyte" (ig). It is preferred that the plants are maize, but any plants—particularly crop plants—which contain haploid-inducing genes are suitable.

The invention further includes the haploid plants, and parts and seeds thereof which result from the use—as a marker in their selection—of a dominant conditional lethal gene, a dominant screenable marker gene, or dominant selectable marker gene. Such haploid off spring are thus easily identified amongst a majority of diploids.

The invention still further includes haploid-inducing plants comprising at least one of a dominant conditional lethal gene, dominant screenable marker gene or a dominant selectable marker gene, particularly androgenetic maize haploids and doubled haploids having the genotypes Ig and IgIg respectively. The invention still further includes plants having a genotype selected from the group consisting of: IgigIaaHIaaH, IgigNiaNia, IgigIaaH-, IgigNia-, igigIaaHIaaH, igigNiaNia, IgigPatPat, IgigGusGus, IgigPat-, IgigGus-, igigPatPat, and igigGusGus.

The invention also includes a process for selecting the genotypes that combine the haploid inducing gene and the conditional lethal gene, screenable gene or selectable gene. The precise details of the process will be obvious to the skilled man, and depend on the genetics of the haploid-inducing factor.

The invention still further includes a process for selecting haploids induced by the indeterminate gametophyte haploid-inducing gene comprising the steps of:

i. Transforming a plant heterozygous for a haploid-inducing gene with a dominant conditional lethal gene;
ii. Selfing the plants resulting from step (i);
iii. Eliminating male sterile plants from the plants resulting from step (ii);
iv. Selfing the plants remaining from step (iii);
v. Discarding plants resulting from step (iv) which are homozygous dominant for the haploid-inducing gene;
vi. Selecting progeny remaining after step (v) which contain the conditional lethal gene;
vii. Selfing the plants selected from step (vi);
viii. Selecting progeny resulting from step (vii) which are homozygous dominant for the conditional lethal gene;
ix. Crossing the plants resulting from step (viii) and selecting plants which are homozygous dominant for the conditional lethal gene and homozygous recessive for the haploid-inducing gene;
x. Pollinating the plants resulting from step (ix) with normal diploid plants; and
xi. Selecting androgenetic haploids and doubled haploids from the plants resulting from step (x).

In the case that screenable marker genes or selectable marker genes are used in the selection of the haploids the process comprises the following steps:

i. Transforming a plant heterozygous for a haploid-inducing gene with a dominant selectable or screenable marker gene;
ii. Selfing the plants resulting from step (i);
iii. Eliminating male sterile plants from the plants resulting from step (ii);
iv. Selfing the plants remaining from step (iii);
v. Discarding plants resulting from step (iv) which are homozygous dominant for the haploid-inducing gene;
vi. Selecting progeny remaining after step (v) which contain the selectable or screenable marker gene;
vii. Selfing the plants selected from step (vi);
viii. Selecting progeny resulting from step (vii) which are homozygous dominant for the selectable or screenable marker gene;
ix. Crossing the plants resulting from step (viii) and selecting plants which are homozygous dominant for the selectable or screenable marker gene and homozygous recessive for the haploid-inducing gene;
x. Pollinating the plants resulting from step (ix) with normal diploid plants; and
xi. Screening or selecting androgenetic haploids and doubled haploids from the plants resulting from step (x).

The invention also includes processes for selecting genotypes that combine genes inducing gynogenetic haploids and the dominant selectable marker, dominant screenable marker, or dominant conditional lethal gene as well as a process for selecting gynogenetic haploids in which the dominant gene in step (i) above is typically introduced into the pollinator line carrying the haploid inducing trait.

The precise details of the processes depend on the genetics of the haploid inducing factor and whether the selectable or screenable marker is introduced into the inducer genotype via sexual crossing or via genetic transformation. In either case the precise details will be obvious to the skilled man.

With the haploid inducing ability governed by dominant genes, introduction of a similarly dominant selectable or screenable marker gene or dominant conditional lethal gene via sexual crossing comprises the following steps:

a. Cross a selected, close-bred "gynogenetic haploid inducer genotype" as female with a genotype homozygous for the selectable or screenable marker gene or conditional lethal gene as the pollen parent.
b. Backcross plants resulting from step (a) to the "gynogenetic haploid inducer genotype".
c. Eliminate plants lacking the selectable or screenable marker gene in the offsprings resulting from step (b).
d. Self a number of the plants retained after step (c).
e. Eliminate plants lacking the selectable or screenable marker gene or conditional lethal gene among progenies resulting from step (d).
f. Cross a number of normal, non-inducer, non-marker plants as females with a corresponding number of plants retained after step (e) as pollen parents. Produce selfed seed from all pollen parents.
g. Use crosses resulting from step (f) to screen pollen parents for homozygosity of the selectable or screenable marker gene or conditional lethal gene as well as for "gynogenetic haploid inducing ability".
h. Remnant selfed seed from pollen parents in step (f), which combine homozygosity for the selectable or screenable marker gene with satisfactory "gynogenetic haploid inducer ability", constitute the desired haploidy inducer stock.

If introducing the selectable or screenable marker gene or conditional lethal gene into the "gynogenetic haploid inducer genotype" via genetic transformation, step (a) above is altered so that a selected, close-bred "gynogenetic haploid inducer genotype" is transformed with a suitable selectable or screenable marker gene or conditional lethal gene and stable transformants are selected.

The invention still further includes haploid-inducing plants, and parts and seeds thereof which result from the said process.

The invention will be further apparent from the following Examples which describe the production and selection of haploid maize plants, and wherein FIGS. 1 and 2 illustrate the genotypes obtained as a consequence of following the breeding schedules disclosed in Examples 1 and 4 respectively.

EXPERIMENTAL

EXAMPLE 1

Use of the IaaH gene in the selection of androgenetic maize haploids and doubled haploids The preferred conditional lethal gene for use in selection of maize hapliods is the gene encoding indoleacetamide hydrolase (IaaH). The IaaH gene is a dominant bacterial gene which determines the final enzymic step in bacterial auxin biosynthesis and is responsible for conversion of indoleacetamide (IAM) to indoleacetic acid (IAA). Tobacco plants carrying the IaaH gene are phenotypically normal. However, if such plants are treated with naphtaleneacetamide (NAM), this substance is converted by the IaaH gene product into naphtaleneacetic acid (NAA) which results in severe growth retardation of the thus treated plants.

For the IaaH gene to be of use as a marker in ig-induced androgenetic haploid production the line carrying the ig gene must be homozygous for IaaH. A suitable haploid-inducing maize line homozygous for the IaaH gene may be produced by the following steps:

1. Place the ig gene in an early maturing, easy to handle genotype with a high level of haploid induction.
2. Transform Igig genotypes with the IaaH gene according to techniques well known to the skilled man, and select a well-functioning transformant.
3. Self transformed plant to produce a segregating $S_1$ generation (see FIG. 1).
4. At flowering time eliminate male sterile plants (homozygous for the igig gene) in the above population.
5. Self all remaining plants.
6. At harvest discard plants having ears with only normal seeds. These are homozygous IgIg-plants.
7. Sow out 20 seeds from each of the remaining progenies and spray seedlings with NAM, thus enabling identification of progenies which lack the IaaH gene (these are not affected by NAM). Such progenies are discarded. Retarded progenies (IgigIaaHIaaH and IgigIaaH- genotypes which occur in the ratio of about 1:2.) are therefore identified and seeds thereof sowed.
8. The plants resulting from 7 are selfed.
9. After harvesting the plants resulting from step 8, 20–30 seeds per plant are sowed out and are and sprayed with NAM. Offspring which segregates for NAM-induced growth retardation are heterozygous for the IaaH gene and are discarded. Progenies which are uniformly growth-retarded originate from the desired genotype IgigIaaHIaaH (flamed in FIG. 1) and are resown using remnant seed.
10. The selected and resown progenies segregate 1:2:1 for the IgIg, Igig and igig. The igig plants are male sterile and are used to reproduce the haploid inducing line. For this purpose crosses are made between a number of the pollen sterile igig plants and pollen fertile sister plants. The crosses are of two kinds:

| a. | igigIaaHIaaH | x | IgIgIaaHIaaH |
|---|---|---|---|
| | ↓ | | |
| 100% IgigIaaHIaaH, all plants pollen fertile and are discarded | | | |
| b. | igigIaaHIaaH | x | IgigIaaHIaaH |
| | ↓ | | |
| | igigIaaHIaaH | : | IgigIaaHIaaH |
| | male sterile | : | pollen fertile |
| | 1 | : | 1 |

11. Through repeated crossings of type (b) above an unlimited number of plants of the igigIaaHIaaH genotype, required for the large scale production of androgenetic haploids, can be produced.
12. When igigIaaHIaaH plants are pollinated by a normal diploid maize population or line all diploid sexual offspring are of the genotype IgigIaaH- and all maternal haploids or doubled haploids of igIaaH and igigIaaHIaaH genotype, respectively. Such plants are all sensitive to NAM treatment and can thus be eliminated. The only offsprings unaffected by the NAM treatment are the desired androgenetic haploids and spontaneously doubled haploids which are of Ig and IgIg genotypes, respectively.

EXAMPLE 2

Use of the nitrate reductase gene (Nia), constitutively expressed, in the selection of androgenetic maize haploids and doubled haploids.

Nitrate reductase (NR), which catalyses the first step of the nitrate assimilation pathway by converting nitrate to nitrite, confers chlorate toxicity. The Nia gene encodes the apoenzyme of NR and tobacco plants transgenic for the Nia gene, constitutively expressed, are phenotypically normal. However such plants are killed if they are grown in medium containing ammonium as the sole carbon source and are treated with chlorate.

Example 1 is thus repeated except that the Igig genotypes in step 2 are transformed with the Nia gene rather than the IaaH gene, and selection is carried out in steps 7, 9 and 12 by treatment with chlorate of plants grown in medium containing ammonium as the sole carbon source.

EXAMPLE 3

Use of a dominant conditional lethal gene as a marker in the selection of gynogenetic maize haploids and doubled haploids.

Examples 1 and 2 describe the production of androgenetic ig-induced haploids wherein an ig-stock transformed with the IaaH gene or the Nia gene is used as the female in crosses with the breeders stock. Examples 1 and 2 are thus repeated except that the haploid-inducing pollinator stock is transformed with the IaaH gene or the Nia gene and is used as the pollinator in crosses with the breeders stock.

EXAMPLE 4

Use of the PAT gene in the selection of androgenetic maize haploids and doubled haploids.

A suitable gene for use as a marker in the selection of maize haploids is that encoding phosphinotricin acetyl transferase (Pat). The Pat gene is a dominant bacterial gene which is responsible for degradation of phosphinotricin. Maize plants carrying the Pat gene are phenotypically normal and when treated with glufosinate they remain healthy in contrast to treated plants lacking this gene.

For the Pat gene to be of use as a marker in ig-induced androgenetic haploid production the line carrying the ig gene must be homozygous for Pat. A suitable haploid-inducing maize line homozygous for the Pat gene may be produced by the following steps:

1. Place the ig gene in an early maturing, easy to handle genotype with a high level of haploid induction.
2. Transform Igig genotypes with the Pat gene according to techniques well known to the skilled man, and select a well-functioning transformant.
3. Self the transformed plant to produce a segregating S1 generation (see FIG. 2). Check glufosinate resistance of the S1 generation by a glufosinate "paint or brush" assay, as is well known to the skilled man. Discard sensitive plants (segregants, unstable transformants or weak Pat-gene expressors).
4. At flowering time eliminate male sterile plants (which are homozygous for the igig gene) in the above population.
5. Self all remaining plants.
6. At harvest discard plants having ears with only normal seeds. These are homozygous IgIg-plants.
7. Sow out all seeds from each of the progenies remaining from step 6 above and when plants obtained therefrom have reached the 4 to 6 leaf stage, spray them with a solution of about 1.5 grams of glufosinate per liter. Several days later, all progenies which lack the PAT gene will have died due to their sensitivity to this herbicide. The remaining progenies (which have IgigPatPat and IgigPat- genotypes which occur in the ratio of about 1:2) are retained.

8. The plants resulting from 7 are selfed.

9. After harvesting the plants resulting from step 8, 20–30 seeds per plant are sowed out and are sprayed with glufosinate. Offspring which segregates for herbicide sensitivity are heterozygous for the Pat gene and are discarded. Progenies which are uniformly herbicide tolerant originate from the desired genotype IgigPatPat (framed in FIG. 2) and are retained.

10. The retained progenies from step 9 segregate 1:2:1 for the IgIg, Igig and igig genes. plants having the genotype igig are male sterile and are used to reproduce the haploid-inducing line. For this purpose crosses are made between a number of the pollen sterile igig plants and pollen fertile sister plants. The crosses are of two kinds:

| a. | igigPatPat | x | IgIgPatPat |
|---|---|---|---|
| | | ↓ | |
| 100% IgigPatPat, all plants pollen fertile and are discarded. | | | |
| b. | igigPatPat | x | IgigPatPat |
| | | ↓ | |
| | igigPatPat | : | IgigPatPat |
| | male sterile | : | pollen fertile |
| | 1 | : | 1 |

11. Through repeated crossings of type (b) above an unlimited number of plants of the igigPatPat genotype, required for the large scale production of androgenetic haploids, is produced.

12. When igigPatPat plants are pollinated by a normal diploid maize population or line, all diploid sexual offspring are of the genotype IgigPat and all maternal haploids or doubled haploids are of the igPat and igigPatPat genotypes, respectively. Such plants are all resistant to glufosinate treatment and can thus be identified and discarded. The only offspring which is sensitive to the herbicide treatment are the desired androgenetic haploids and spontaneously doubled haploids which have the Ig and IgIg genotypes, respectively. To recover the herbicide sensitive haploid and doubled haploid plantlets, the herbicide is to be used on a fraction of the plant only, preferably a leaf tip applied by either spray or brush in a concentration of about 1.5 grams glufosinate per liter. Sensitive plants are easily recognized several days post application by necrosis and subsequent desiccation of the leaf tip. The plants, damage to each of which is localized to the leaf tip only, develop further and are fertile if chromosome doubling occurs.

EXAMPLE 5

Use of the Beta-glucuronidase gene, constitutively expressed, in the screening of androgenetic maize haploids and doubled haploids Example 4 is repeated except that the Pat gene is replaced by that encoding Beta glucuronidase (GUS) which is capable of cleaving a glucuronide optionally comprising a plant growth regulator or other component which when cleaved from the glucuronide is chromogenic, flurogenic or otherwise easily capable of being recognized by the man skilled in the art.

1. The GUS gene is best expressed by an embryo-specific promoter as expression of the GUS gene in the endosperm should be avoided. This in necessary as an androgenetic haploid or doubled haploid can, with a certain frequency, develop in association with an endosperm which arose from one of the female bipolar nuclei in the ovule. GUS expression by the endosperm would thus mask the non-expressing androgenetic haploid or doubled haploid embryo and produce a GUS false positive score.

2. The Igig genotypes in step 2 of Example 4 are transformed with the Beta-glucuronidase gene rather than the Pat gene, and screening is carried out on seeds in steps 7, 9 and 12 by making a small incision in the pericarp of the seed in order to allow the glucuronide substrate to diffuse to the embryo. In the case that the glucuronide comprises a component capable of fluorescing, for example, once it is cleaved by Beta glucuronidase from the glucuronide diploid embryos can be identified by their fluorescence due to expression of the introduced GUS gene. In contrast thereto, androgenetic haploid embryos will lack the GUS trait and will not be fluorescent. In any case, distinction between the different cell types is easily made according to known techniques, including autoradiography or spectroscopy.

EXAMPLE 6

Use of a dominant selectable or screenable gene as a marker in the selection of gynogenetic maize haploids and doubled haploids.

Examples 4 and 5 describe the production of androgenetic/g-induced haploids wherein an ig-stock transformed with the Pat gene or the GUS gene is used as the female in crosses with the breeders stock. Examples 4 and 5 are thus repeated except that a haploid-inducing pollinator stock is transformed with Pat gene or the GUS gene and is used as the pollinator in crosses with the breeders stock.

It will be appreciated that the invention is not limited to the selection of maize haploids (either androgenic or gynogenetic) as described above, but is applicable to the selection of haploids in other plants, particularly crop plants, which contain haploid-inducing genes. Moreover, any suitable dominant selectable or screenable marker gene may be substituted for the Pat or GUS genes respectively, and likewise any suitable dominant conditional lethal gene may be substituted for the IaaH and Nia genes.

It will be further appreciated that the dominant genes may be used in the selection of haploids at specific developmental stages. In this regard it is particularly preferred that the said genes are under the control of a promoter functional in the embryo thus enabling haploid selection at the seed, rather than whole plant, level (as is exemplified above).

We claim:

1. A process for selecting maize haploids induced by a haploid-inducing gene comprising the steps of:
   i. Transforming a maize plant heterozygous for a haploid-inducing gene with a dominant conditional lethal gene;
   ii. Selfing the plants resulting from step (i);
   iii. Eliminating male sterile plants from the plants resulting from step (ii);
   iv. Selfing the plants remaining from step (iii);
   v. Discarding plants resulting from step (iv) which are homozygous dominant for the haploid-inducing gene;
   vi. Selecting progeny remaining after step (v) which contain the conditional lethal gene;

vii. Selfing the plants selected from step (vi);

viii. Selecting progeny resulting from step (vii) which are homozygous dominant for the conditional lethal gene;

ix. Crossing the plants resulting from step (viii) and selecting maize plants which are homozygous dominant for the conditional lethal gene and homozygous recessive for the haploid-inducing gene;

x. Pollinating the plants resulting from step (ix) with normal diploid plants; and xi. Selecting androgenetic haploids and doubled haploids from the maize plants resulting from step (x).

2. A process for selecting maize haploids induced by a haploid-inducing gene comprising the steps of:

i. Transforming a maize plant heterozygous for a haploid-inducing gene with a dominant selectable or screenable marker gene;

ii. Salting the plants resulting from step (i);

iii. Eliminating male sterile plants from the plants resulting from step (ii);

iv. Selfing the plants remaining from step (iii);

v. Discarding plants resulting from step (iv) which are homozygous dominant for the haploid-inducing gene;

vi. Selecting progeny remaining after step (v) which contain the selectable or screenable marker gene;

vii. Selfing the plants selected from step (vi);

viii. Selecting progeny resulting from step (vii) which are homozygous dominant for the selectable or screenable marker gene;

ix. Crossing the plants resulting from step (viii) and selecting plants which are homozygous dominant for the selectable or screenable marker gene and homozygous recessive for the haploid-inducing gene;

x. Pollinating the plants resulting from step (ix) with normal diploid plants; and xi. Screening or selecting androgenetic haploids and doubled haploids from the maize plants resulting from step (x).

3. A process according to claim 1, wherein the haploid inducing gene is an indeterminate gametophyte.

4. A process according to claim 2, wherein the haploid inducing gene is an indeterminate gametophyte.

5. A process according to claim 1, wherein the conditional lethal gene confers sensitivity to a chemical.

6. A process according to claim 5, wherein the chemical is selected from the group consisting of chlorate, naphthaleneacetamide and indole-3-acetamide.

7. A process according to claim 2, wherein the selectable gene confers resistance or tolerance to a herbicide or antibiotic and the screenable gene encodes a protein capable of cleaving a chromogenic or fluorogenic substrate.

8. A process according to claim 7, wherein the selectable gene encodes phosphinotricin acetyl transferase (PAT), glyphosate oxido-reductase (GOX) or EPSPS, and the screenable gene encodes Beta-glucuronidase.

9. A process according to claim 6, wherein the lethal gene encodes indoleacetamide hydrolase (IaaH) or nitrate reductase (NR).

10. A process according to claim 2, wherein the selectable gene encodes phosphinotricin acetyl transferase (PAT), glyphosate oxido-reductase (GOX) or EPSPS, and the screenable gene encodes Beta-glucuronidase.

11. A process according to claim 3, wherein gynogenetic haploids are capable of being selected by introduction of the dominant gene of step (i) into the pollinator line carrying the haploid inducing trait.

12. A process according to claim 3, wherein gynogenetic haploids are capable of being selected by introduction of the dominant gene of step (i) into the pollinator line carrying the haploid inducing trait.

13. A process according to claim 11, wherein the pollinator line has a genotype capable of inducing gynogenetic haploids at a frequency of greater than about 0.1%.

14. A process according to claim 12, wherein the pollinator line has a genotype capable of inducing gynogenetic haploids at a frequency of greater than about 0.1%.

15. A process according to claim 13, wherein the frequency is about 0.5%.

16. A process according to claim 14, wherein the frequency is about 0.5%.

17. A process according to claim 11, wherein the dominant conditional lethal gene is introduced into the pollinator line carrying the haploid inducing gene.

18. A process according to claim 12, wherein the dominant conditional lethal gene is introduced into the pollinator line carrying the haploid inducing gene.

19. Haploid-inducing maize plants comprising at least one of a dominant conditional lethal gene, dominant screenable marker gene or a dominant selectable gene and having a genotype selected from the group consisting of: IgigIaaHIaaH, IgigNiaNia, IgigIaaH-, IgigNia-, igigIaaHIaaH, igigNiaNia, IgigPatPat, IgigGusGus, IgigPat-, IgigGus-, igigPatPat, and igigGusGus.

20. A process for selecting gynogenetic maize haploids comprising a dominant selectable or screenable marker gene or dominant conditional lethal gene comprising the following steps:

a. Crossing a selected, close-bred gynogenetic haploid inducer genotype as a female with a genotype homozygous for the selectable or screenable marker gene or conditional lethal gene as the pollen parent, or alternatively transform said haploid inducer genotype with a selectable or screenable marker gene or conditional gene and select stable transformants;

b. Backcrossing maize plants resulting from step (a) to the gynogenetic haploid inducer genotype;

c. Eliminating plants lacking the selectable or screenable marker gene in the offsprings resulting from step (b);

d. Selfing a number of the maize plants retained after step (c);

e. Eliminating plants lacking the selectable or screenable marker gene or conditional lethal gene among progenies resulting from step (d);

f. Crossing a number of normal, non-inducer, non-marker plants as females with a corresponding number of plants retained after step (e) as pollen parents and producing selfed seed from all pollen parents;

g. Using crosses resulting from step (f) to screen pollen parents for homozygosity of the selectable or screenable marker gene or conditional lethal gene as well as for gynogenetic haploid inducing ability; and h. Selecting the desired haploidy inducer stock from remnant selfed seed from pollen parents in step (f), which combine homozygosity for the selectable or screenable marker gene with satisfactory gynogenetic haploid inducer ability.

21. Haploid maize plants, or parts or seeds thereof, each which result from the process according to claim 1.

22. Haploid maize plants, or parts or seeds thereof, each which result from the process according to claim 2.

23. Androgenetic or gynogentic maize haploids having the genotype Ig, or androgenetic or gynogenetic maize doubled haploids having the genotype IgIg, each being selected by a process comprising the use of a dominant conditional lethal gene, a dominant selectable marker gene or a dominant screenable marker gene.

* * * * *